US008632486B2

(12) United States Patent
Muller (10) Patent No.: US 8,632,486 B2
(45) Date of Patent: *Jan. 21, 2014

(54) ELECTROMAGNETIC INDUCTION ACCESS DISCONNECT SYSTEMS

(75) Inventor: Matthew R. Muller, Lindenhurst, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 24 days.

This patent is subject to a terminal disclaimer.

(21) Appl. No.: 13/343,484

(22) Filed: Jan. 4, 2012

(65) Prior Publication Data

US 2012/0101422 A1     Apr. 26, 2012

Related U.S. Application Data

(63) Continuation of application No. 12/180,318, filed on Jul. 25, 2008, now Pat. No. 8,114,043.

(51) Int. Cl.
*A61M 37/00* (2006.01)

(52) U.S. Cl.
USPC .................. 604/6.04; 604/6.01; 604/6.09

(58) Field of Classification Search
USPC ........ 604/4.01–6.16, 65, 67; 210/85, 87, 103, 210/645–646
See application file for complete search history.

(56) References Cited

U.S. PATENT DOCUMENTS

| 3,618,602 A | 11/1971 | Shaw |
| 3,659,591 A | 5/1972 | Doll et al. |
| 3,682,162 A | 8/1972 | Colyer |
| 3,682,172 A | 8/1972 | Freedman et al. |
| 3,699,960 A | 10/1972 | Freedman |
| 3,722,504 A | 3/1973 | Sawyer |
| 3,731,685 A | 5/1973 | Eidus |
| 3,744,636 A | 7/1973 | Commarmot |
| 3,759,247 A | 9/1973 | Doll et al. |

(Continued)

FOREIGN PATENT DOCUMENTS

| AU | 199896231 | 3/1999 |
| CA | 2 175 903 | 5/1995 |

(Continued)

OTHER PUBLICATIONS

Mexican Office Action issued Jan. 17, 2012 for related Mexican Appln. No. MX/a/2011/000978.
A Noninvasive Peripheral Blood Flow Monitor which Uses Electromagnetic Induction, Aori Akira, et al., vol. 74, No. 11, dated 2004, pp. 653-660.
International Search Report and Written Opinion for Internatinal Application No. PCT/US2009/047581 mailed Sep. 25, 2009.

(Continued)

*Primary Examiner* — Philip R Wiest
(74) *Attorney, Agent, or Firm* — K&L Gates LLP (57) ABSTRACT

An access disconnect system includes a blood processing machine having a blood pump operable with blood tubing, first and second conductive contacts located in the blood tubing on an arterial tubing side of a blood filter. The first conductive contact is located upstream of the blood pump and the second conductive contact is located downstream of the blood pump. The first and second conductive contacts are positioned and arranged to form a conductive circuit including a vascular system of a patient and the blood processing machine. The system further includes a source of electric current connected to at least one of the first and second conductive contacts and a transmitter for sending a signal indicative of an amount of current flowing through the conductive circuit when the source of electric current is applied.

20 Claims, 5 Drawing Sheets

(56) References Cited

U.S. PATENT DOCUMENTS

| | | |
|---|---|---|
| 3,759,261 A | 9/1973 | Wang |
| 3,778,570 A | 12/1973 | Shuman |
| 3,809,078 A | 5/1974 | Mozes |
| 3,810,140 A | 5/1974 | Finley |
| 3,814,249 A | 6/1974 | Eaton |
| 3,832,067 A | 8/1974 | Kopf et al. |
| 3,832,993 A | 9/1974 | Clipp |
| 3,864,676 A | 2/1975 | Macias et al. |
| 3,878,095 A | 4/1975 | Frasier et al. |
| 3,882,861 A | 5/1975 | Kettering et al. |
| 3,900,396 A | 8/1975 | Lamadrid |
| 3,946,731 A | 3/1976 | Lichtenstein |
| 3,953,790 A | 4/1976 | Ebling et al. |
| 3,979,665 A | 9/1976 | Ebling et al. |
| 4,010,749 A | 3/1977 | Shaw |
| 4,017,190 A | 4/1977 | Fischel |
| 4,022,211 A | 5/1977 | Timmons et al. |
| 4,026,800 A | 5/1977 | Friedrich et al. |
| 4,055,496 A | 10/1977 | Friedrich et al. |
| 4,060,485 A | 11/1977 | Eaton |
| 4,085,047 A | 4/1978 | Thompson |
| 4,087,185 A | 5/1978 | Lamadrid |
| 4,160,946 A | 7/1979 | Frigato |
| 4,162,490 A | 7/1979 | Fu et al. |
| 4,166,961 A | 9/1979 | Dam et al. |
| 4,167,038 A | 9/1979 | Hennessy |
| 4,181,610 A | 1/1980 | Shintani et al. |
| 4,191,950 A | 3/1980 | Levin et al. |
| 4,192,311 A | 3/1980 | Felfoldi |
| 4,193,068 A | 3/1980 | Ziccardi |
| 4,194,974 A | 3/1980 | Jonsson |
| 4,231,366 A | 11/1980 | Schael |
| 4,231,370 A | 11/1980 | Mroz et al. |
| 4,269,708 A | 5/1981 | Bonomini et al. |
| 4,294,263 A | 10/1981 | Hochman |
| 4,295,475 A | 10/1981 | Torzala |
| 4,303,887 A | 12/1981 | Hill et al. |
| 4,324,687 A | 4/1982 | Louderback et al. |
| 4,327,731 A | 5/1982 | Powell |
| 4,353,368 A | 10/1982 | Slovák et al. |
| 4,354,504 A | 10/1982 | Bro |
| 4,366,051 A | 12/1982 | Fischel |
| 4,399,823 A | 8/1983 | Donnelly |
| 4,399,824 A | 8/1983 | Davidson |
| 4,450,527 A | 5/1984 | Sramek |
| 4,484,573 A | 11/1984 | Yoo |
| 4,501,583 A | 2/1985 | Troutner |
| 4,510,489 A | 4/1985 | Anderson, III et al. |
| 4,534,756 A | 8/1985 | Nelson |
| 4,539,559 A | 9/1985 | Kelly et al. |
| 4,566,990 A | 1/1986 | Liu et al. |
| 4,583,546 A | 4/1986 | Garde |
| 4,648,869 A | 3/1987 | Bobo, Jr. |
| 4,661,096 A | 4/1987 | Teeple |
| 4,710,163 A | 12/1987 | Butterfield |
| 4,734,198 A | 3/1988 | Harm et al. |
| 4,739,492 A | 4/1988 | Cochran |
| 4,741,343 A | 5/1988 | Bowman et al. |
| 4,796,014 A | 1/1989 | Chia |
| 4,846,792 A | 7/1989 | Bobo, Jr. |
| 4,862,146 A | 8/1989 | McCoy et al. |
| 4,881,413 A | 11/1989 | Georgi et al. |
| 4,898,587 A | 2/1990 | Mera |
| 4,923,613 A | 5/1990 | Chevallet |
| 4,931,051 A | 6/1990 | Castello |
| 4,941,870 A | 7/1990 | Okada et al. |
| 4,959,060 A | 9/1990 | Shimomura et al. |
| 4,965,554 A | 10/1990 | Darling |
| 4,966,729 A | 10/1990 | Carmona et al. |
| 4,976,698 A | 12/1990 | Stokley |
| 4,977,906 A | 12/1990 | Di Scipio |
| 4,979,940 A | 12/1990 | Bobo, Jr. |
| 4,981,467 A | 1/1991 | Bobo, Jr. et al. |
| 5,004,459 A | 4/1991 | Peabody et al. |
| 5,015,958 A | 5/1991 | Masia et al. |
| 5,024,756 A | 6/1991 | Sternby |
| 5,026,348 A | 6/1991 | Venegas |
| 5,030,487 A | 7/1991 | Rosenzweig |
| 5,030,497 A | 7/1991 | Claessen |
| 5,036,859 A | 8/1991 | Brown |
| 5,084,026 A | 1/1992 | Shapiro |
| 5,088,990 A | 2/1992 | Hivale et al. |
| 5,100,374 A | 3/1992 | Kageyama |
| 5,121,630 A | 6/1992 | Calvin |
| 5,137,033 A | 8/1992 | Norton |
| 5,139,482 A | 8/1992 | Simeon et al. |
| 5,145,645 A | 9/1992 | Zakin et al. |
| 5,146,414 A | 9/1992 | McKown et al. |
| 5,197,958 A | 3/1993 | Howell |
| 5,202,261 A | 4/1993 | Musho et al. |
| 5,211,201 A | 5/1993 | Kamen et al. |
| 5,247,434 A | 9/1993 | Peterson et al. |
| 5,248,934 A | 9/1993 | Roveti |
| 5,250,439 A | 10/1993 | Musho et al. |
| 5,264,830 A | 11/1993 | Kline et al. |
| 5,266,928 A | 11/1993 | Johnson |
| 5,291,181 A | 3/1994 | DePonte |
| 5,310,507 A | 5/1994 | Zakin et al. |
| 5,314,410 A | 5/1994 | Marks |
| 5,341,127 A | 8/1994 | Smith |
| 5,354,289 A | 10/1994 | Mitchell et al. |
| 5,389,093 A | 2/1995 | Howell |
| 5,392,032 A | 2/1995 | Kline et al. |
| 5,395,358 A | 3/1995 | Lu |
| 5,399,295 A | 3/1995 | Gamble et al. |
| 5,427,695 A | 6/1995 | Brown |
| 5,431,496 A | 7/1995 | Balteau et al. |
| 5,435,010 A | 7/1995 | May |
| 5,439,442 A | 8/1995 | Bellifemine |
| 5,454,374 A | 10/1995 | Omachi |
| 5,468,236 A | 11/1995 | Everhart et al. |
| 5,469,145 A | 11/1995 | Johnson |
| 5,486,286 A | 1/1996 | Peterson et al. |
| 5,487,827 A | 1/1996 | Peterson et al. |
| 5,509,822 A | 4/1996 | Negus et al. |
| 5,522,809 A | 6/1996 | Larsonneur |
| 5,542,932 A | 8/1996 | Daugherty |
| 5,557,263 A | 9/1996 | Fisher et al. |
| 5,567,320 A | 10/1996 | Goux et al. |
| 5,568,128 A | 10/1996 | Nair |
| 5,570,082 A | 10/1996 | Mahgerefteh et al. |
| 5,571,401 A | 11/1996 | Lewis et al. |
| 5,603,902 A | 2/1997 | Maltais et al. |
| 5,644,240 A | 7/1997 | Brugger |
| 5,645,734 A | 7/1997 | Kenley et al. |
| 5,649,914 A | 7/1997 | Glaug et al. |
| 5,670,050 A | 9/1997 | Brose et al. |
| 5,674,390 A | 10/1997 | Matthews et al. |
| 5,674,752 A | 10/1997 | Buckley et al. |
| 5,681,298 A | 10/1997 | Brunner et al. |
| 5,690,610 A | 11/1997 | Ito et al. |
| 5,690,624 A | 11/1997 | Sasaki et al. |
| 5,690,821 A | 11/1997 | Kenley et al. |
| 5,698,089 A | 12/1997 | Lewis et al. |
| 5,702,376 A | 12/1997 | Glaug et al. |
| 5,702,377 A | 12/1997 | Collier, IV et al. |
| 5,718,692 A | 2/1998 | Schon et al. |
| 5,730,418 A | 3/1998 | Feith et al. |
| 5,744,027 A | 4/1998 | Connell et al. |
| 5,760,694 A | 6/1998 | Nissim et al. |
| 5,762,805 A | 6/1998 | Truitt et al. |
| 5,766,212 A | 6/1998 | Jitoe et al. |
| 5,779,657 A | 7/1998 | Daneshvar |
| 5,788,833 A | 8/1998 | Lewis et al. |
| 5,790,035 A | 8/1998 | Ho |
| 5,790,036 A | 8/1998 | Fisher et al. |
| 5,796,345 A | 8/1998 | Leventis et al. |
| 5,797,892 A | 8/1998 | Glaug et al. |
| 5,800,386 A | 9/1998 | Bellifemine |
| 5,802,814 A | 9/1998 | Sano |
| 5,803,915 A | 9/1998 | Kremenchugsky et al. |
| 5,813,432 A | 9/1998 | Elsdon et al. |
| 5,817,076 A | 10/1998 | Fard |
| 5,838,240 A | 11/1998 | Johnson |

(56) References Cited

U.S. PATENT DOCUMENTS

| | | |
|---|---|---|
| 5,842,998 A | 12/1998 | Gopakumaran et al. |
| 5,845,644 A | 12/1998 | Hughes et al. |
| 5,847,639 A | 12/1998 | Yaniger |
| 5,862,804 A | 1/1999 | Ketchum |
| 5,863,421 A | 1/1999 | Peter, Jr. et al. |
| 5,868,723 A | 2/1999 | Al-Sabah |
| 5,885,264 A | 3/1999 | Matsushita |
| 5,891,398 A | 4/1999 | Lewis et al. |
| 5,900,726 A | 5/1999 | Brugger et al. |
| 5,900,817 A | 5/1999 | Olmassakian |
| 5,903,222 A | 5/1999 | Kawarizadeh et al. |
| 5,904,671 A | 5/1999 | Navot et al. |
| 5,908,411 A | 6/1999 | Matsunari |
| 5,911,706 A | 6/1999 | Estabrook et al. |
| 5,911,872 A | 6/1999 | Lewis et al. |
| 5,931,801 A | 8/1999 | Burbank et al. |
| 5,932,110 A | 8/1999 | Shah et al. |
| 5,935,077 A | 8/1999 | Ogle |
| 5,938,038 A | 8/1999 | Ziberna |
| 5,941,248 A | 8/1999 | Wheeler |
| 5,947,943 A | 9/1999 | Lee |
| 5,954,691 A | 9/1999 | Prosl |
| 5,954,951 A | 9/1999 | Nuccio |
| 5,959,535 A | 9/1999 | Remsburg |
| 6,009,339 A | 12/1999 | Bentsen et al. |
| 6,038,914 A | 3/2000 | Carr et al. |
| 6,044,691 A | 4/2000 | Kenley et al. |
| 6,063,042 A | 5/2000 | Navot et al. |
| 6,069,564 A | 5/2000 | Hatano et al. |
| 6,071,421 A | 6/2000 | Brown |
| 6,075,178 A | 6/2000 | La Wilhelm et al. |
| 6,077,443 A | 6/2000 | Goldau |
| 6,090,048 A | 7/2000 | Hertz et al. |
| 6,093,869 A | 7/2000 | Roe et al. |
| 6,097,297 A | 8/2000 | Fard |
| 6,113,577 A | 9/2000 | Hakky |
| 6,123,847 A | 9/2000 | Bene |
| 6,136,201 A | 10/2000 | Shah et al. |
| 6,143,181 A | 11/2000 | Falkvall et al. |
| 6,149,636 A | 11/2000 | Roe et al. |
| 6,154,137 A | 11/2000 | Goff et al. |
| 6,160,198 A | 12/2000 | Roe et al. |
| 6,166,639 A | 12/2000 | Pierce et al. |
| 6,167,765 B1 | 1/2001 | Weitzel |
| 6,169,225 B1 | 1/2001 | Otsubo |
| 6,171,289 B1 | 1/2001 | Millot et al. |
| 6,187,199 B1 | 2/2001 | Goldau |
| 6,200,250 B1 | 3/2001 | Janszen |
| 6,206,851 B1 | 3/2001 | Prosl |
| 6,208,880 B1 | 3/2001 | Bentsen et al. |
| 6,210,591 B1 | 4/2001 | Kriritski |
| 6,217,539 B1 | 4/2001 | Goldau |
| 6,221,040 B1 | 4/2001 | Kleinekofort |
| 6,255,396 B1 | 7/2001 | Ding et al. |
| 6,309,673 B1 | 10/2001 | Duponchelle et al. |
| 6,319,243 B1 | 11/2001 | Becker et al. |
| 6,325,774 B1 | 12/2001 | Bene et al. |
| 6,331,244 B1 | 12/2001 | Lewis et al. |
| 6,372,848 B1 | 4/2002 | Yang et al. |
| 6,387,329 B1 | 5/2002 | Lewis et al. |
| 6,397,661 B1 | 6/2002 | Grimes et al. |
| 6,402,207 B1 | 6/2002 | Segal et al. |
| 6,406,460 B1 | 6/2002 | Hogan |
| 6,452,371 B1 | 9/2002 | Brugger |
| 6,461,329 B1 | 10/2002 | Van Antwerp et al. |
| 6,500,154 B1 | 12/2002 | Hakky et al. |
| 6,509,217 B1 | 1/2003 | Reddy |
| 6,561,996 B1 | 5/2003 | Gorsuch |
| 6,565,525 B1 | 5/2003 | Burbank et al. |
| 6,572,576 B2 | 6/2003 | Brugger et al. |
| 6,575,927 B1 | 6/2003 | Weitzel et al. |
| 6,582,397 B2 | 6/2003 | Alesi et al. |
| 6,585,675 B1 | 7/2003 | O'Mahoney et al. |
| 6,595,942 B2 | 7/2003 | Kleinekofort |
| 6,612,624 B1 | 9/2003 | Segal et al. |
| 6,623,443 B1 | 9/2003 | Polaschegg |
| 6,623,638 B2 | 9/2003 | Watkins |
| 6,663,585 B1 | 12/2003 | Ender |
| 6,736,789 B1 | 5/2004 | Spickermann |
| 6,752,785 B2 | 6/2004 | Van Antwerp et al. |
| 6,767,333 B1 | 7/2004 | Müller et al. |
| 6,804,991 B2 | 10/2004 | Balschat et al. |
| 6,827,698 B1 | 12/2004 | Kleinekofort |
| 6,880,404 B2 | 4/2005 | Überreiter |
| 6,897,809 B2 | 5/2005 | Carson et al. |
| 6,924,733 B1 | 8/2005 | McTier et al. |
| 6,932,786 B2 | 8/2005 | Giacomelli et al. |
| 6,962,580 B2 | 11/2005 | Adams et al. |
| 6,979,306 B2 | 12/2005 | Moll |
| 7,011,855 B2 | 3/2006 | Martis et al. |
| 7,022,098 B2 | 4/2006 | Wariar et al. |
| 7,040,142 B2 | 5/2006 | Burbank |
| 7,050,047 B2 | 5/2006 | Hong |
| 7,052,480 B2 | 5/2006 | Han et al. |
| 7,053,059 B2 | 5/2006 | Zieske |
| 7,053,781 B1 | 5/2006 | Haire et al. |
| 7,056,316 B1 | 6/2006 | Burbank et al. |
| 7,059,518 B2 | 6/2006 | Forster |
| 7,060,047 B2 | 6/2006 | Lodi et al. |
| 7,070,591 B2 | 7/2006 | Adams et al. |
| 7,087,033 B2 | 8/2006 | Brugger et al. |
| 7,102,572 B2 | 9/2006 | Okado |
| 7,138,088 B2 | 11/2006 | Wariar et al. |
| 7,170,414 B2 | 1/2007 | Clifford et al. |
| 7,172,569 B2 | 2/2007 | Kleinekofort |
| 7,172,570 B2 | 2/2007 | Cavalcanti et al. |
| 7,537,687 B2 | 5/2009 | Toyoda et al. |
| 8,114,043 B2 * | 2/2012 | Muller .......... 604/6.04 |
| 2001/0004523 A1 | 6/2001 | Bosetto et al. |
| 2002/0036375 A1 | 3/2002 | Matsuda |
| 2002/0042125 A1 | 4/2002 | Petersen et al. |
| 2002/0055167 A1 | 5/2002 | Pourahmadi et al. |
| 2002/0088752 A1 | 7/2002 | Balschat et al. |
| 2002/0120260 A1 | 8/2002 | Morris et al. |
| 2002/0120261 A1 | 8/2002 | Morris et al. |
| 2002/0121471 A1 | 9/2002 | Pedrazzi |
| 2002/0141901 A1 | 10/2002 | Lewis et al. |
| 2002/0162778 A1 | 11/2002 | Peabody et al. |
| 2002/0173731 A1 | 11/2002 | Martin et al. |
| 2002/0188206 A1 | 12/2002 | Davis et al. |
| 2002/0190839 A1 | 12/2002 | Padmanabhan et al. |
| 2002/0197390 A1 | 12/2002 | Lewis et al. |
| 2002/0198483 A1 | 12/2002 | Wariar et al. |
| 2003/0009123 A1 | 1/2003 | Brugger et al. |
| 2003/0016002 A1 | 1/2003 | Brugger et al. |
| 2003/0036719 A1 * | 2/2003 | Giacomelli et al. ......... 604/5.04 |
| 2003/0075498 A1 | 4/2003 | Watkins et al. |
| 2003/0083901 A1 | 5/2003 | Bosch et al. |
| 2003/0093069 A1 | 5/2003 | Panescu et al. |
| 2003/0094369 A1 | 5/2003 | Tolley et al. |
| 2003/0126910 A1 | 7/2003 | Burbank |
| 2003/0128125 A1 | 7/2003 | Burbank et al. |
| 2003/0128126 A1 | 7/2003 | Burbank et al. |
| 2003/0138501 A1 | 7/2003 | Elisabettini et al. |
| 2003/0152482 A1 | 8/2003 | O'Mahony et al. |
| 2003/0176829 A1 | 9/2003 | Lodi et al. |
| 2003/0194894 A1 * | 10/2003 | Wariar et al. ............ 439/191 |
| 2003/0195453 A1 | 10/2003 | Han et al. |
| 2003/0195454 A1 | 10/2003 | Wariar et al. |
| 2004/0009096 A1 | 1/2004 | Wellman |
| 2004/0054352 A1 | 3/2004 | Adams et al. |
| 2004/0113801 A1 | 6/2004 | Gustafson et al. |
| 2004/0185709 A1 | 9/2004 | Williams, Jr. et al. |
| 2004/0186409 A1 | 9/2004 | Cavalcanti et al. |
| 2004/0186415 A1 | 9/2004 | Burbank et al. |
| 2004/0201216 A1 | 10/2004 | Segal et al. |
| 2004/0212504 A1 | 10/2004 | Forcier et al. |
| 2004/0243046 A1 | 12/2004 | Brugger et al. |
| 2005/0010118 A1 | 1/2005 | Toyoda et al. |
| 2005/0010157 A1 | 1/2005 | Baraldi et al. |
| 2005/0038325 A1 | 2/2005 | Moll |
| 2005/0096578 A1 | 5/2005 | Kleinekofort |
| 2005/0131332 A1 | 6/2005 | Kelly et al. |
| 2005/0230313 A1 | 10/2005 | O'Mahony et al. |

(56) References Cited

U.S. PATENT DOCUMENTS

| | | |
|---|---|---|
| 2005/0241387 A1 | 11/2005 | Miesel et al. |
| 2005/0245858 A1 | 11/2005 | Miesel et al. |
| 2005/0256451 A1 | 11/2005 | Adams et al. |
| 2005/0256457 A1 | 11/2005 | Rome |
| 2006/0012774 A1 | 1/2006 | O'Mahony et al. |
| 2006/0069339 A1 | 3/2006 | Moll |
| 2006/0087120 A1 | 4/2006 | Segal et al. |
| 2006/0097920 A1 | 5/2006 | Lin et al. |
| 2006/0116623 A1* | 6/2006 | Han et al. .............. 604/4.01 |
| 2006/0130591 A1 | 6/2006 | Perkins |
| 2006/0166548 A1 | 7/2006 | Williams, Jr. et al. |
| 2006/0184087 A1 | 8/2006 | Wariar et al. |
| 2007/0004996 A1 | 1/2007 | Lovejoy et al. |
| 2007/0096919 A1 | 5/2007 | Knadle, Jr. et al. |
| 2007/0128174 A1 | 6/2007 | Kleinsek et al. |
| 2008/0015494 A1 | 1/2008 | Santini, Jr. et al. |
| 2008/0065006 A1 | 3/2008 | Roger |
| 2008/0108930 A1 | 5/2008 | Weitzel et al. |
| 2008/0195021 A1 | 8/2008 | Roger |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2010/0022934 A1 | 1/2010 | Hogard |

FOREIGN PATENT DOCUMENTS

| | | |
|---|---|---|
| CA | 2 282 628 | 11/2006 |
| DE | 28 38 414 | 3/1980 |
| DE | 29 48 768 | 6/1981 |
| DE | 30 45 514 | 7/1982 |
| DE | 32 23 086 | 7/1983 |
| DE | 34 40 584 | 5/1986 |
| DE | 38 23 859 | 1/1990 |
| DE | 38 36 712 | 5/1990 |
| DE | 40 00 961 | 7/1991 |
| DE | 40 14 572 | 11/1991 |
| DE | 40 18 953 | 1/1992 |
| DE | 40 23 336 | 2/1992 |
| DE | 42 39 937 | 6/1994 |
| DE | 19 72 8031 | 1/1999 |
| DE | 19 73 9099 | 1/1999 |
| DE | 19 90 1078 | 2/2000 |
| EP | 0 270 048 | 6/1988 |
| EP | 0 272 414 | 6/1988 |
| EP | 0 287 485 | 10/1988 |
| EP | 0 328 162 | 8/1989 |
| EP | 0 328 163 | 8/1989 |
| EP | 0 332 330 | 9/1989 |
| EP | 0 259 551 | 9/1990 |
| EP | 0 542 140 | 5/1993 |
| EP | 0 551 043 | 7/1993 |
| EP | 0 472 798 | 3/1994 |
| EP | 0 584 557 | 3/1994 |
| EP | 0 590 810 | 4/1994 |
| EP | 0 611 228 | 8/1994 |
| EP | 0 745 400 | 12/1996 |
| EP | 0 820 776 | 1/1998 |
| EP | 0 835 669 | 4/1998 |
| EP | 0 846 470 | 6/1998 |
| EP | 0 895 787 | 2/1999 |
| EP | 0 898 975 | 3/1999 |
| EP | 0 898 976 | 3/1999 |
| EP | 0 911 044 | 4/1999 |
| EP | 0 930 080 | 7/1999 |
| EP | 0 943 369 | 9/1999 |
| EP | 1 156 841 | 11/2001 |
| EP | 1 401 518 | 3/2006 |
| EP | 2318072 B1 | 8/2012 |
| FR | 2 680 678 | 5/1993 |
| FR | 2 737 124 | 1/1997 |
| GB | 2 069 702 | 8/1981 |
| GB | 2 145 859 | 3/1985 |
| GB | 2 177 247 | 1/1987 |
| GB | 2 250 121 | 5/1992 |
| GB | DE 19 74 6367 | 6/1998 |
| GB | DE 10 10 0146 | 7/2002 |
| JP | 55-031407 | 3/1980 |
| JP | 57-044845 | 3/1982 |
| JP | 62-042047 | 2/1987 |
| JP | 62-54157 | 3/1987 |
| JP | 64-052473 | 2/1989 |
| JP | 01250733 | 10/1989 |
| JP | 4008361 | 1/1992 |
| JP | 6178789 | 6/1994 |
| JP | 10-201842 | 4/1998 |
| JP | 10211278 | 8/1998 |
| JP | 11-104233 | 4/1999 |
| JP | 11-267197 | 10/1999 |
| JP | 11299889 | 11/1999 |
| JP | 2000-140092 | 5/2000 |
| JP | 2000131286 | 5/2000 |
| JP | 2006055588 | 3/2006 |
| JP | 2006110118 | 4/2006 |
| WO | WO 81/00295 | 2/1981 |
| WO | WO 86/04710 | 8/1986 |
| WO | WO 89/12228 | 12/1989 |
| WO | WO 94/02918 | 2/1994 |
| WO | WO 94/07224 | 3/1994 |
| WO | WO 95/12545 | 5/1995 |
| WO | WO 96/25904 | 8/1996 |
| WO | WO 9702057 | 1/1997 |
| WO | WO 97/03712 | 2/1997 |
| WO | WO 97/10013 | 3/1997 |
| WO | WO 98/32476 | 7/1998 |
| WO | WO 98/38485 | 9/1998 |
| WO | WO 99/12588 | 3/1999 |
| WO | WO 99/24145 | 5/1999 |
| WO | WO 99/26686 | 6/1999 |
| WO | WO 99/29356 | 6/1999 |
| WO | WO 99/42151 | 8/1999 |
| WO | WO 00/38761 | 7/2000 |
| WO | WO 01/06975 | 2/2001 |
| WO | WO 01/24854 | 4/2001 |
| WO | WO 01/47581 | 7/2001 |
| WO | WO 02/098543 | 12/2002 |
| WO | WO 02/102441 | 12/2002 |
| WO | WO 03/000315 | 1/2003 |
| WO | WO 03/006944 | 1/2003 |
| WO | WO 03/086504 | 10/2003 |
| WO | WO 03/086505 | 10/2003 |
| WO | WO 03/086506 | 10/2003 |
| WO | WO 2004/082740 | 9/2004 |
| WO | WO 2004/084972 | 10/2004 |
| WO | WO 2004/108192 | 12/2004 |
| WO | WO 2004/108206 | 12/2004 |
| WO | WO 2005/019416 | 3/2005 |
| WO | WO 2005/046439 | 5/2005 |
| WO | WO 2005/105199 | 11/2005 |
| WO | WO 2005/105200 | 11/2005 |
| WO | WO 2006/001759 | 1/2006 |
| WO | WO 2006/088419 | 8/2006 |
| WO | WO 2008/023388 | 2/2008 |
| WO | WO 2008/028653 | 3/2008 |
| WO | WO 2009/042262 | 4/2009 |

OTHER PUBLICATIONS

International Preliminary Report on Patentability for International Application No. PCT/US2009/047581 mailed on Oct. 28, 2010.

* cited by examiner

ELECTROMAGNETIC INDUCTION ACCESS DISCONNECT SYSTEMS

PRIORITY CLAIM

This application claims priority to and the benefit as a continuation application of U.S. patent application entitled, "Electromagnetic Induction Access Disconnect Sensor", Ser. No. 12/180,318, filed Jul. 25, 2008, the entire contents of which are incorporated herein by reference and relied upon.

BACKGROUND

The invention is in the field of medical treatments generally and patient vascular access systems. The present invention relates to embodiments for detecting blood leakage during extracorporeal blood treatment or other medical procedure.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from complications that can arise from continuing therapeutic procedures, and even from diagnostic procedures, that are necessary for their continued care. Treatments involving extra-corporeal blood treatment are clear examples.

The most obvious danger is infection, but the harm caused by infection can be overcome by not re-using even supposedly-sterile devices, by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421. There are also other related procedures, such as hemofiltration or hemodiafiltration in which needle dislodgement should be avoided in order to safeguard the health of the patient.

The extracorporeal medical treatments described above require that the blood be removed for treatment and then returned. This requires access to the patient's vascular system, from which blood is removed and to which blood is then returned. If a "batch" treatment is used, that is, if a quantity of blood is withdrawn, treated and returned, only a single needle is used. Each batch in such a treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle. Other treatments are continuous, such as the platelet separation discussed above, dialysis treatment, or a heart-lung bypass operation, and may require a duration of several hours or even overnight.

Continuous treatments require two needles, or access points, one for withdrawal of blood and one for return. The withdrawal site is normally an artery or an arteriovenous fistula/graft, and a needle and a pump are used to provide the blood to the therapeutic machine. It is relatively simple to detect a problem with withdrawal, for instance if the withdrawal needle is dislodged, using conventional air sensor technology. Detecting a problem in the return of the blood to the patient is more difficult. The return line typically includes a needle with venous access. If the return line is dislodged, the blood is not returned to the patient's vascular system, but may continue to be pumped and may accumulate near the patient. Depending on the pumping rate of the blood and the time for treatment, this could have life-threatening effects on the patient within a very short period of time.

Accordingly, a number of apparatuses have been devised for detecting needle dislodgement, especially venous needle dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. For example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

SUMMARY

The embodiments described herein overcome numerous of the disadvantages and problems in the prior art. One embodiment is a method for detecting an access disconnect. The method includes steps of generating a time-varying electric current in a vascular system of a patient and an extracorporeal blood circuit with conductive connections in at least one of the vascular system of the patient and the extracorporeal blood circuit, monitoring a value of a quantity corresponding to the electric current with a non-contact sensor atop an access site of the patient, near the vascular system of the patient or near tubing of the extracorporeal blood circuit, comparing the value with preselected limits for the value, and sending a signal if the value exceeds the preselected limits.

Another embodiment is a method for detecting an access disconnect. The method includes steps of generating a time-varying electric current in a vascular system of a patient and an extracorporeal blood circuit with at least one conductive connection, monitoring a value of a quantity corresponding to the electric current with a non-contact sensor atop an access site of the patient, near the vascular system of the patient, or near tubing of the extracorporeal blood circuit, comparing the value with preselected limits for the value, and sending a signal if the value exceeds the preselected limits.

Another embodiment is an access disconnect system. The system includes a conductive connection between a vascular system of a patient and a hemodialysis machine, the conductive connection including first and second conductive contacts in tubing leading to and from the hemodialysis machine. The system also includes a source of time-varying electric current connected to said first conductive contact, a non-contact sensor for positioning atop an access site of the patient, near the vascular system of the patient, or near the tubing, the non-contact sensor configured for detecting a value of a quantity corresponding to the current, and a transmitter operably connected to the non-contact sensor for sending a signal indicative of the value to a controller of the hemodialysis machine.

Another embodiment is an access disconnect system. The access disconnect system includes a conductive connection between a vascular system of a patient and a hemodialysis machine, the conductive connection including first and second conductive contacts in tubing leading to the hemodialysis machine, a source of time-varying electric current connected to said first conductive contact, a non-contact sensor for positioning atop an access site of the patient, near the vascular system of the patient, or near the tubing, the non-contact sensor configured for detecting a value of a quantity corresponding to the current, and a transmitter operably connected to the non-contact sensor for sending a signal indicative of the value to a controller of the hemodialysis machine.

Additional features and advantages are described herein, and will be apparent from the following Detailed Description and the figures.

DETAILED DESCRIPTION

Figure 1:
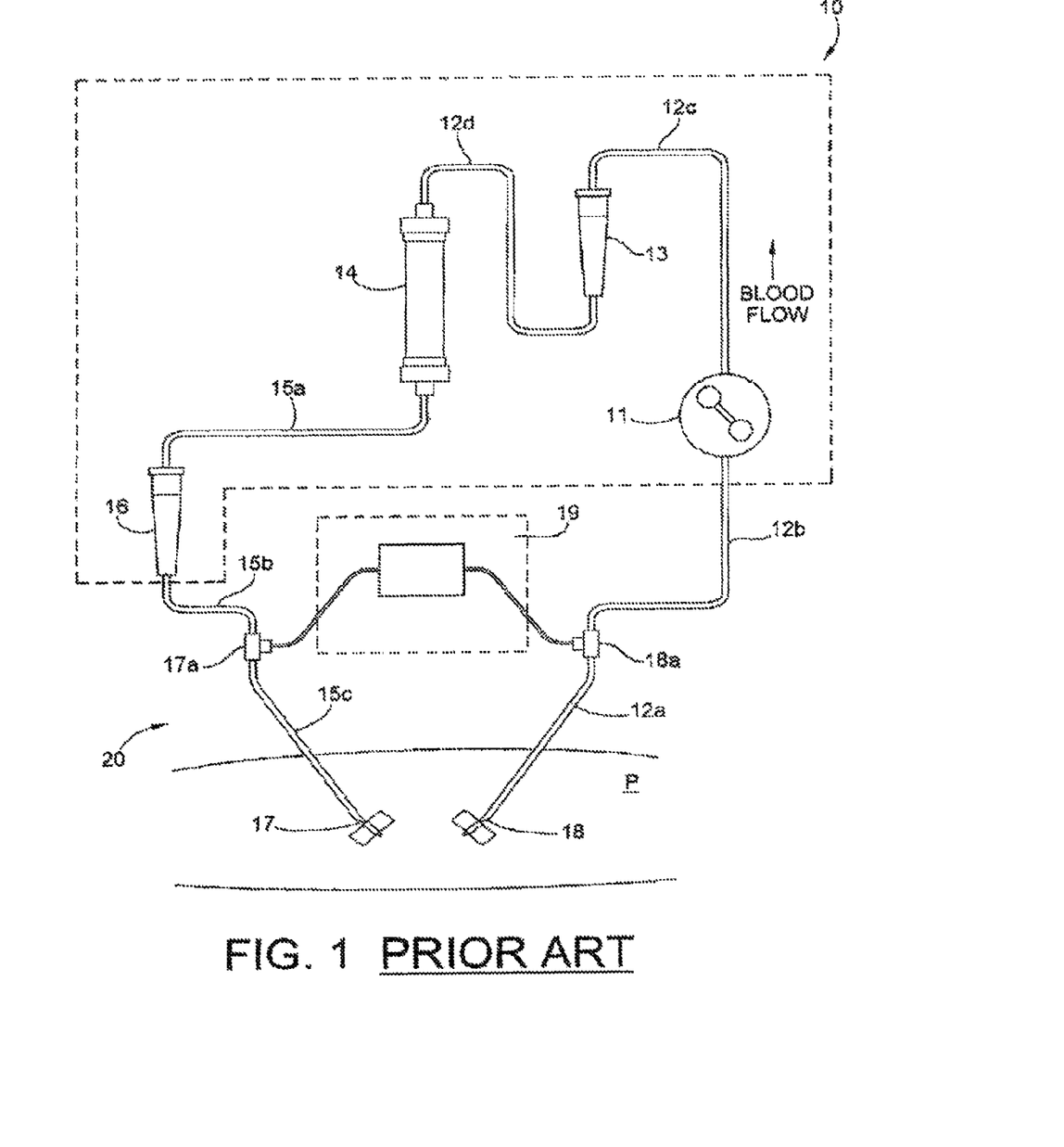
FIG. 1 is a schematic depiction of a prior art hemodialysis machine with an access disconnect system.

The advantages of the improvements are described in detail herein. FIG. 1 depicts a prior art hemodialysis system in which there are no access disconnects sensors or alarms. The main portions of the hemodialysis machine 10 are enclosed with the dotted-line enclosure. These include a blood pump 11, for connection to an arterial access of the patient P, such as arterial needle 18 and arterial tubing 12a, 12b for drawing blood to blood pump 11. The blood is then pumped through tubing 12c to an arterial drip chamber 13 and thence through tubing 12d to dialyzer 14. Those having skill in the art will recognize that arterial drip chamber 13 is optional and that tubing portions 12a-12d may be a single length of medically-acceptable tubing. These portions define the arterial or upstream portion of the extracorporeal blood circuit, that is, upstream of the dialyzer or blood treatment device 14.

Downstream of the dialyzer 14, the venous or downstream portion of the extracorporeal blood circuit includes venous drip chamber 16, the tubing portion 15a that leads from the dialyzer to the drip chamber, and tubing portions 15b and 15c. Tubing portion 15b leads from drip chamber 16 to venous clamp 17a and tubing portion 15c leads from venous clamp 17a to the venous access needle 17. A system controller 19 controls an on/off position of venous clamp 17a and arterial clamp 18a. These clamps allow a caregiver to stop the flow of blood if there is a disconnect of the venous needle 17 or the arterial needle 18. In this system, however, direct observation of the needle is required to detect such a disconnect or leakage of blood from the tubing or from the patient. A switch or button on the hemodialysis controller 19 is then pressed to actuate one or both of the line clamps.

Figure 2:
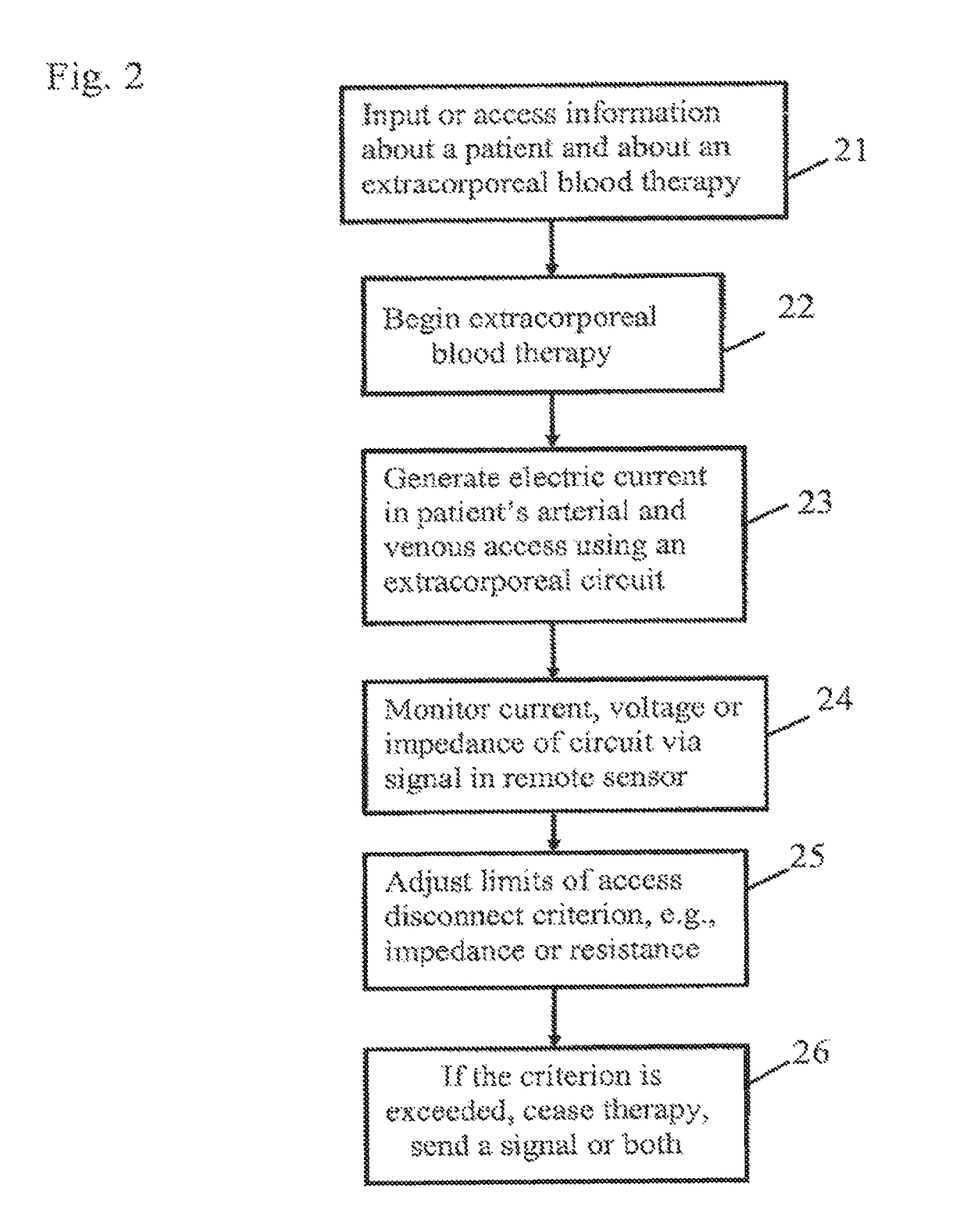
FIG. 2 is a flowchart for a method of detecting an access disconnect with a remote or non-contact electromagnetic sensor.

A method for administering a hemodialysis procedure according to the present disclosure is depicted in the flowchart of FIG. 2. In this method, a medical professional, a caregiver, or the patient himself or herself accesses the machine and inputs information 21 about a desired procedure, such as the patient name, specific protocol, and so forth. An extracorporeal blood treatment or therapy is begun 22 by connecting the patient to the machine with secure arterial and venous access in the usual manner and then switching on the machine. In this method, a very small and safe electric current is generated 23 in the extracorporeal blood circuit, and in a portion of the patient's vasculature. One example is an arteriovenous fistula of the patient, into which the venous and arterial needles are inserted. The electric current is generated by an electric signal generator and by electric contacts in direct contact with blood of the patient or in a conductive connection to blood of the patient, e.g., a capacitive connection. The capacitive connection may be formed by a metallic conductor on the outside of the tubing, as one plate of a capacitor and the blood of the patient as the opposite plate, with the tubing forming the dielectric portion of the capacitor between the metallic conductor and the blood of the patient. Blood is known to conduct electricity.

The electric current described above is then generated, using alternating current at a very low voltage and a very low current, i.e., a few microamperes, less than 10 microamperes. The current is then monitored 24 by tracking at least one electrical parameter that correlates with current in the circuit. The current itself may be monitored, with a decrease in current suggesting that the circuit has been interrupted, perhaps by the venous or arterial access needle slipping from the patient access site. Other parameters may instead be tracked, such as the voltage used to maintain a nominal current, or the impedance or conductivity of the circuit itself.

Even though blood is a conductor of electricity, the conductivity of blood of patients can vary enormously. In addition, the blood itself may be undergoing a procedure that directly affects the conductivity of the blood, e.g., dialysis or plasmapheresis. Thus, after the electric circuit has been energized and a safe current has been established, the parameters or criteria for safe and undisturbed operation of the access disconnect circuit are established 25. These may include limits on the current itself, e.g., plus or minus so many microamperes, or on the voltage needed to maintain the expected current, e.g., plus or minus so many volts. If the current rises below or above these limits, or the voltage rises above or below these limits, the system controller can alert the patient or a caregiver to the condition. Alternatively, the impedance of the circuit or its inverse, the circuit conductivity, may be used, and limits on either of these set as the limits for the access disconnect system.

If these limits are exceeded, the access disconnect system sends a signal 26 to the hemodialysis machine to cease therapy. Alternatively, the signal may sent to an alarm output, such as a nearby speaker or computer screen, that an abnormal condition has occurred, so that the patient or a caregiver can take appropriate action. The patient or caregiver may check for needle disconnect, actuate an arterial or venous line clamp, stop the blood pump, or any combination of these actions. The system may also be configured so that one or more of these actions is taken automatically by the hemodialysis machine controller when the signal is sent or when the value of the appropriate parameter is exceeded. After the signal is given or the machine ceases its operation, the medical professional, caregiver, or patient can check the access disconnect system, or the hemodialysis machine, to see what caused the parameter to exceed the expected value, and to take corrective action. It is understood that while a primary use for this method occurs in hemodialysis, the method is also applicable to other extracorporeal blood treatments, such as plasmapheresis and apheresis. It may also be applied to other protocols, such as heart-lung bypass operations, in which the blood is withdrawn from the patient's venous access and returned to the patient's arterial access.

Figure 3:
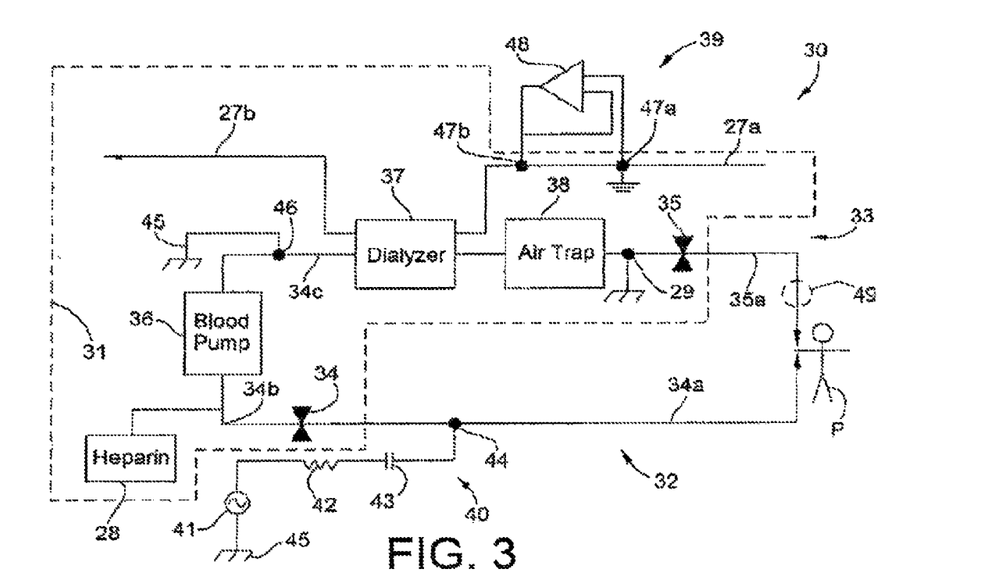
FIG. 3 is a first embodiment of a system for detecting an access disconnect according to the method of FIG. 2.

Systems embodying these improvements are now described. A first embodiment is depicted in FIG. 3. Hemodialysis and access disconnect system 30 includes a hemodialysis machine 31 (enclosed in dashed lines) and additional components as shown. The patient P is connected to an extracorporeal blood circuit that includes arterial side 32, which extends from the patient's arterial access needle (not shown) to the inlet to the dialyzer 37. The arterial side 32 includes arterial blood tubing 34a, 34b, and arterial line clamp 34. The venous side 33 extends from the patient's venous access needle (not shown) to the outlet of the dialyzer 37. The venous side also includes venous tubing 35a and venous line clamp 35.

Hemodialysis machine 31 includes blood pump 36 and arterial tubing 34c extending from the blood pump 36 to the inlet of the dialyzer 37. The arterial side also includes heparin pump 28 for administering small amounts of anti-coagulant heparin to the blood near the inlet of the blood pump 36. The access disconnect portion of the system includes a generator 41, a current limiting resistor 42, and a filtering capacitor 43, all connected to a direct electrical contact 44 in arterial tubing 34a. The current limiting resistor in one embodiment has a value from about 100 kilohm to about 1 megohm. The filtering capacitor, which prevents DC voltage reaching the patient, typically has a value of about 1 although other capacitances may instead be used. The generator has a return to a chassis or other local ground 45. Another contact for the access disconnect is second contact 46, also located on the arterial side, between the blood pump 36 and the inlet to the dialyzer 37. Second contact 46 is also a direct contact with the tubing 34c, and in contact with first contact 44 through chassis ground 45 and the generator 41 circuit. In one embodiment contacts 44, 46 are metallic contacts extending through the tubing and directly into the blood, i.e., disposable. In another embodiment, contacts 44, 46 may be capacitive contacts on the outside of the tubing for conductive connections thereto, but since they are not in direct contact with the blood, are not disposable but are reusable.

Generator 41 outputs standard, sine-wave alternating current at low voltage and low current. In other embodiments, a square wave, a saw-tooth, or other wave form may be used. In operation, generator 41 generates a current that conducts through current-limiting resistor 42 and filtering capacitor 43 to first contact 44. The current then typically does not conduct through the blood pump 36 because of its very high resistance or impedance. Instead, currently flows through the blood in tubing 34a, through a part of the vasculature of patient P, through the blood of venous tubing 35a air trap or bubble chamber 38 and then through the dialyzer 37 to first contact 46. The current returns through the local or chassis grounds 45 as shown. This embodiment also includes an optional current preventing or guard circuit 39 as part of the dialyzer 37 dialysate tubing. Dialyzer 37 includes inlet tubing 27a carrying fresh dialysate to the dialyzer and outlet tubing 27b removing spent dialysate from the dialyzer. The guard circuit includes an operation amplifier 48 connected as a voltage follower between contacts 47a, 47b on the inlet tubing 27a. A voltage follower has an output with virtually the same voltage as its input. With the voltage the same at both contact points 47a, 47b, virtually no current can flow in the dialyzer tubing, and thus one source of error or extra current is eliminated.

It has been unexpectedly found that the electrical impedance of blood pump 36 is very high, while the combined impedance of the air trap 38 and the dialyzer 37 are lower than expected. Thus, a good circuit can be formed, and a reliable current path established, between contact 44 and contact 46, even though both are on the "arterial" side, i.e., upstream of dialyzer 37. Note that the current path is not upstream of the dialyzer, but rather extends from the generator 41, through first contact 44, through tubing 34a, the patient P, venous tubing 35a, drip chamber 38, and the dialyzer 37, to second contact 46. Alternatively, the current path may be formed using venous contact 29, in this example between the bubble trap 38 and the venous line clamp 35, instead of the second arterial contact 46.

The current thus generated is detected by a sensor 49 worn by the patient P near the venous access site and venous needle, the sensor 49 sensing the current in a non-contact manner. The sensor thus detects the current via an electromagnetic coupling, such as by magnetic induction, using a hall-effect sensor, an electromagnetic induction coil, a capacitance sensor, or other non-contact detection principle. In order to minimize the burden on the patient, and to give the patient as much freedom of movement as possible, the sensor 49 may communicate with the hemodialysis machine, and its controller, in a wireless manner, e.g., with a very small, very light-weight radio transmitter also worn by the patient and connected to the sensor. Details of this connection are disclosed below.

Figure 4:
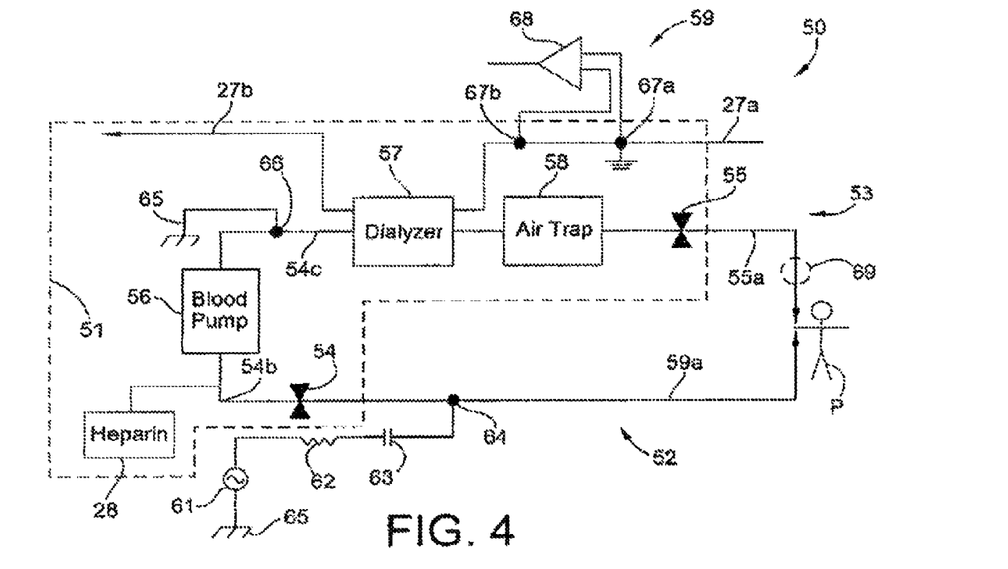
FIG. 4 is a second embodiment of a system for detecting an access disconnect according to the method of FIG. 2.

A second embodiment of a system using such contacts and the sensor is depicted in FIG. 4. Hemodialysis and access disconnect system 50 includes a hemodialysis machine 51 (enclosed in dashed lines) and additional components as shown. The patient P is connected to an extracorporeal blood circuit that includes arterial side 52, which extends from the patient's arterial access needle (not shown) to the inlet to the dialyzer 57. The arterial side 52 includes arterial blood tubing 54a, 54b, 54c, and arterial line clamp 54. The venous side 53 extends from the patient's venous access needle (not shown) to the outlet of the dialyzer 57. The venous side also includes venous tubing 55a and venous line clamp 55.

Hemodialysis machine 51 includes blood pump 56 and arterial tubing 54c extending from the blood pump 56 to the inlet of the dialyzer 57. The arterial side also includes heparin pump 28 for administering small amounts of anti-coagulant heparin to the blood near the inlet of the blood pump 56. The access disconnect portion of the system includes a generator 61, a current limiting resistor 62, and a filtering capacitor 63, all connected to a direct electrical contact 64 in the arterial tubing 54a. The generator has a return to a chassis or other local ground 65. Another contact for the access disconnect is second contact 66, also located on the arterial side, between the blood pump 36 and the inlet to the dialyzer 37. Second contact 66 is also in direct contact with the tubing 54c, and in contact with first contact 64 through chassis ground 65 and the generator 61 circuit. In one embodiment contacts 64, 66 are metallic contacts extending through the tubing and directly into the blood, i.e., disposable. In another embodiment, contacts 64, 66 may be capacitive contacts on the outside of the tubing for conductive connections thereto, but since they are not in direct contact with the blood, are not disposable but are reusable.

Generator 61 outputs standard, sine-wave alternating current at low voltage and low current. In other embodiments, a square wave, a saw-tooth, or other wave form may be used. In operation, generator 61 generates a current that conducts through current-limiting resistor 62 and filtering capacitor 63 to first contact 64. The current then typically does not conduct through the blood pump 56 because of its very high resistance or impedance. Instead, currently flows through the blood in tubing 54a, through a part of the vasculature of patient P, through the blood of venous tubing 55a, through air trap or bubble chamber 58 and then through the dialyzer 57 to first contact 66. The current returns through the local or chassis grounds 65 as shown.

This embodiment also includes an optional current sensing circuit 59 as part of the dialyzer 57 dialysate tubing. Dialyzer 57 includes inlet tubing 27a carrying fresh dialysate to the dialyzer and outlet tubing 27b removing spent dialysate from the dialyzer. The sensing circuit includes an operation amplifier 68 connected between contacts 67a, 67b on the inlet tubing 27a. This circuit senses the current flowing through the dialysate tubing and generates a sense signal, the sense signal sent to the controller (not shown) of the hemodialysis machine or the access disconnect system. Knowing the current, an operator or caregiver has indications of the machine health and currents that might interfere with proper operation of the machine or care of the patient. Hemodialysis machine 51 and hemodialysis machine and access disconnect system 50 operate in a manner similar to that of the embodiment of FIG. 3.

Figure 5:
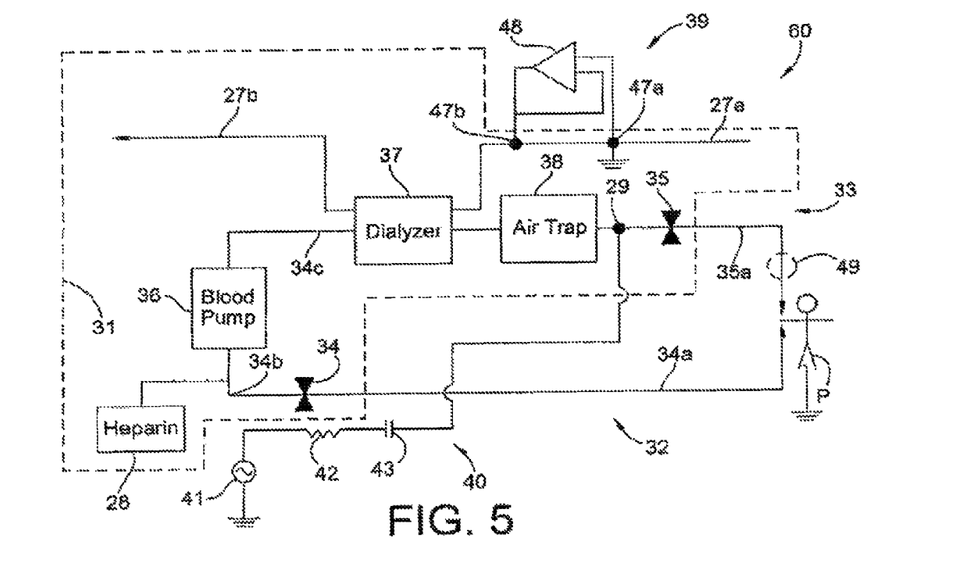
FIG. 5 is a third embodiment of a system for detecting an access disconnect.

Another embodiment of an electromagnetic induction access disconnect sensor is depicted in FIG. 5. In this embodiment, the hemodialysis machine with an access disconnect system 60 is very similar to the hemodialysis machine 31 of FIG. 3, with an arterial side 32 and a venous side 33. The arterial side 32 includes arterial blood tubing 34a, 34b, and arterial line clamp 34. The venous side 33 extends from the patient's venous access needle (not shown) to the outlet of the dialyzer 37. The venous side also includes venous tubing 35a, venous line clamp 35, and air trap 38. Hemodialysis machine 31 includes blood pump 36 and arterial tubing 34c extending from the blood pump 36 to the inlet of the dialyzer 37. The arterial portion also includes heparin pump 28 for administering small amounts of anti-coagulant heparin to the blood near the inlet of the blood pump 36.

The access disconnect portion of the system includes a generator 41, a current limiting resistor 42, and a filtering capacitor 43, all connected to a single direct electrical contact 29 in the venous tubing. The current limiting resistor in one embodiment has a value from about 100 kilohm to about 1 megohm. The filtering capacitor, which prevents DC voltage reaching the patient, typically has a value of about 1 µF, although other capacitances may instead be used. The generator has a return to an earth ground. In this system, the patient P is also connected to an earth ground to complete the current circle. This detection system functions in a very similar way to that described above for the hemodialysis machine, i.e., a current or voltage is injected into the venous contact, the current traveling through the venous blood tubing and the patient's cardiovascular system, with a return to ground.

In one embodiment of an access disconnect system, a relatively constant, low voltage alternating current is used, and the current is switched on and detected periodically, rather than continuously. For example, the current may be switched on for 5 seconds every minute. If the current is not switched on, or if the switched-on current or voltage is not detected, the controller, described below, can determine the discrepancy and send a signal to alert the patient or a caregiver.

Figure 6:
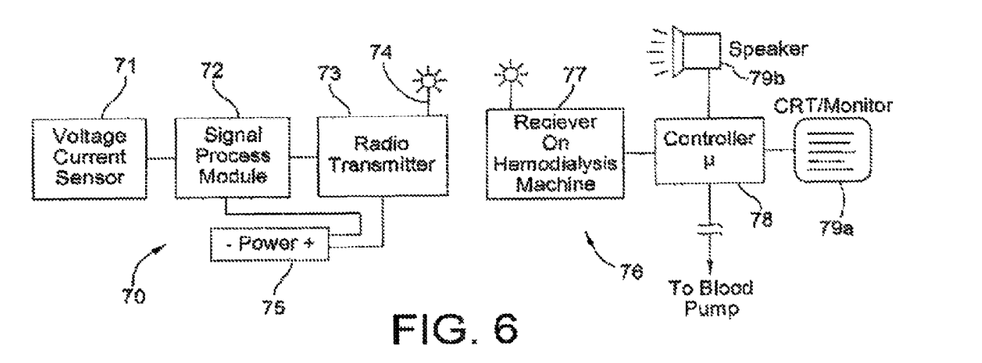
FIG. 6 is a schematic depiction of a non-contact access disconnect detection sensor and associated hardware.

The sensors and detection circuits used in these embodiments are depicted in FIG. 6. Detection circuit 70 includes a voltage or current sensor 71, as discussed above. This may be an electromagnetic induction coil, a capacitive sensor, a hall-effect sensor, and so forth. In the circuit, a power supply or battery 75 operates a sensor controller/signal processing module 72 and also a small radio transmitter 73 and antenna 74. The current is detected by the sensor as controlled by the signal processing module 72. The detected current, or a value of a quantity indicative of the current or the circuit, is then transmitted by the radio 73 to the hemodialysis machine controller circuit 76. The controller circuit 76 includes a radio receiver 77 with an antenna and a microcontroller 78. The microcontroller 78 includes at least one look-up table of expected values of parameters of the detected values of the quantity associated with the current. If the reported value is outside the acceptable limits of the range of the quantity, the microcontroller will note and record the discrepancy, and alert the patient or a caregiver of that fact. The alert is given by sending a signal to an output of the hemodialysis machine, such as a computer screen 79a or a local speaker 79b. Of course, the machine may also cause one or both of the arterial and venous clamps to close and also shut off the blood pump.

The signal processing circuitry and wireless transmitter are small and compact, and are easily placed on the patient at the access site. One module that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The module may include a power supply and an ADC converter to convert analog data from the sensor into digital data. The digital data is thus formatted, at least by the sensor, before transmission to the controller of the hemodialysis machine or other extracorporeal processing machine controller.

The hemodialysis controller is very near, within range of the ZigBee module, about 10-20 feet at most. Thus, the signal module is conveniently small and unobtrusive for the patient. As noted, the hemodialysis machine includes a radio receiver for receiving transmissions from the patient radio transmitter. The hemodialysis machine also includes signal processing circuitry for processing the signal data and a microprocessor or microcontroller for interpreting the processed data.

The microcontroller of the hemodialysis machine or other machine also includes a computer program and logic for interpreting the processed signals and for determining a next step. If the processed signals suggest that the value of the current, or other quantity is within bounds, then the hemodialysis machine controller takes no action. The processed signals, however, may suggest a change, such as an interruption of the current, a rise in the voltage, or an increase in the impedance. If this happens, the data may be recorded in a memory of the hemodialysis machine, and a signal may be sent as a result of the detection of a value of the quantity. The signal may cause an alarm to be sounded to alert the patient or medical personnel to the condition. The signal may instead or in addition send a signal to the hemodialysis machine or blood processing machine to cease pumping blood from the patient, or to close one or both of the blood tubing clamps. In other applications, the signal may cause other appropriate actions to be taken to alert one or more personnel and to cease whatever medical procedure is taking place to avoid harm to the patient.

Figure 7:
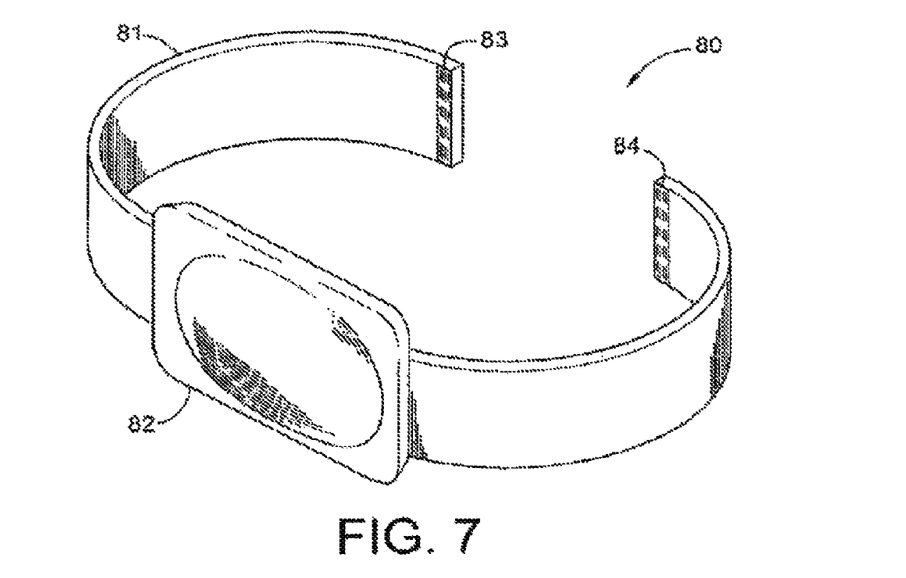
FIG. 7 is a perspective view of a wristband for a patient incorporating the sensor and associated circuitry and FIG. 8 is a perspective view of a sensor directly applied to a patient.

In one embodiment, the sensor described above is mounted atop the access site, over the blood vessel containing the venous needle, or over the tubing. In this embodiment, the sensor, the associated circuitry, and a battery are mounted to a small housing on a wristband worn by the patient. FIG. 7 depicts the wristband-mounted sensor 80, including a wristband 81, housing 82, and hook-and-loop fasteners 83, 84. The sensor and associated circuitry, such as those depicted in FIG. 5, are mounted within housing 82 so as to be as close as possible to the undersurface of the housing and near the skin of the patient near the access site or the blood tubing. After connecting the patient to the extracorporeal blood treatment machine, the patient or a caregiver mounts the wristband with the underside of the housing near the access site or the tubing, and then begins the treatment.

It is also possible to mount the sensor, the radio transmitter, and the power supply in a very small adhesive-backed housing. The housing will have an outer layer of adhesive; alternatively, the sensor may be secured over the venous branch of the blood tubing with a layer of tape. The sensor/housing is placed a short distance away from the venous needle and the blood vessel containing the venous needle, such as atop the access site or over the tubing, so that the sensor is held very near the point of blood return to the patient. The blood is conducting a few microamps of current for detection by the sensor, and thus at least the bottom wall of the housing is kept thin and non-metallic, so as not to impede detection of the current.

Figure 8:
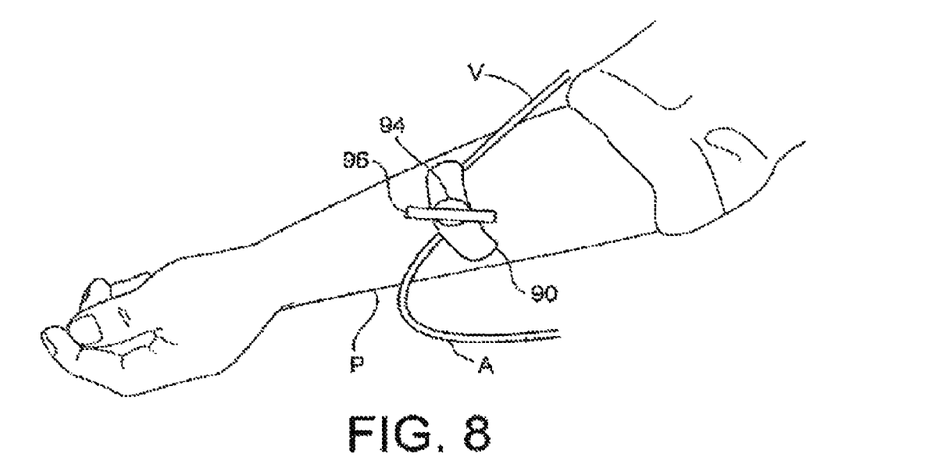

In one embodiment, as shown in FIG. 8, the sensor 94 and its housing looks like a larger version of an ECG or EEG electrode, but will be somewhat thicker and larger because the housing also holds a small transmitter and a power supply. FIG. 8 also depicts a patient P with an access site 90 and arterial tubing A and venous access tubing V. The sensor 94 with its housing is mounted atop the access site 90 or atop the venous tubing V with a strip of adhesive tape 96. Note that some transmitters, with associated electronics, are now the size of a quarter-dollar or smaller. These technologies make it possible to use an ultra-small sensor for detecting the current and transmitting the instantaneous current, or other detected readings, to the hemodialysis machine. In one embodiment, a conductive gel, similar to that used for EEG electrodes, to encourage better electrical coupling, may be applied between the housing and the tubing and skin of the patient.

It will be understood by those having skill in the art that the sensor and its output could as well be connected by a thin wire harness to the hemodialysis or other machine. Using a radio link as described above, however, has extra advantages and convenience for patients, who have limited freedom of movement even with the radio link described herein. Other changes will also be readily envisioned by those with skill in the art, and are intended to be covered by the claims below.

Various changes and modifications to the embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. An access disconnect system comprising:
    blood tubing including a blood filter and an arterial tubing side of the blood filter;
    a blood processing machine including a blood pump operable with the blood tubing;
    first and second conductive contacts located in the blood tubing on the arterial tubing side of the blood filter, the first conductive contact located upstream of the blood pump, and the second conductive contact located downstream of the blood pump, the first and second conductive contacts positioned and arranged to enable a conductive circuit to be formed with a vascular system of a patient and the blood processing machine;
    a source of electric current connected to at least one of the first and second conductive contacts;
    a sensor configured to sense an amount of electric current flowing through the conductive circuit when the source of electric current is applied; and
    a transmitter for sending a signal indicative of an amount of current sensed by the sensor flowing through the conductive circuit when the source of electric current is applied.

2. The access disconnect system of claim 1, wherein the sensor includes a non-contact sensor for positioning atop an access site of the patient, near the vascular system of the patient, or near the blood tubing, the non-contact sensor configured for sensing the amount of electric current, and wherein the transmitter is operably connected to the non-contact sensor.

3. The access disconnect system according to claim 2, wherein the non-contact sensor is selected from the group consisting of a hall-effect sensor, an induction coil, a capacitive sensor and an induction sensor.

4. The access disconnect system of claim 1, wherein the blood processing machine includes a controller and the signal is sent to the controller.

5. The access disconnect system of claim 4, wherein the controller is programmed to determine whether the signal is within preselected limits.

6. The access disconnect system of claim 1, wherein if the signal falls outside of a preselected limit, the blood processing machine is configured to automatically (i) actuate a line clamp, or (ii) stop the blood pump.

7. The access disconnect system according to claim 1, wherein the electric current source is a time varying electric current source, and the electric current is ten microamperes or less.

8. The access disconnect system according to claim 1, wherein the transmitter is positioned at the access site of the patient.

9. An access disconnect system comprising:
    blood tubing including a blood filter and an arterial tubing side of the blood filter;
    a blood processing machine including a blood pump operable with the blood tubing;
    first and second conductive contacts in the blood tubing on the arterial tubing side of the blood filter, the first conductive contact located upstream of the blood pump and the second conductive contact located downstream of the blood pump, the first and second conductive contacts positioned and arranged to enable a conductive circuit to be formed with a vascular system of a patient and the blood processing machine;
    a source of electric current connected to at least one of the first and second conductive contacts;
    a sensor configured to sense an amount of electric current flowing through the conductive circuit when the source of electric current is applied; and
    a wireless transmitter for sending a signal indicative of an amount of current sensed by the sensor flowing through the conductive circuit when the source of electric current is applied.

10. The access disconnect system of claim 9, wherein the sensor includes a non-contact sensor mounted to a wristband and for positioning atop an access site of the patient or near the vascular system of the patient, the non-contact sensor configured for the amount of electric current, and wherein the wireless transmitter is operably connected to the non-contact sensor.

11. The access disconnect system of claim 10, wherein the non-contact sensor operates using electrical capacitance, inductance, or magnetic coupling.

12. The access disconnect system of claim 9, wherein the blood pump the blood processing machine is configured to automatically issue an alert if the signal falls outside of a preselected limit.

13. The access disconnect system of claim 9, wherein the blood processing machine includes a line clamp for clamping the blood tubing based upon the signal sent from the transmitter.

14. The access disconnect system of claim 9, which includes a current sensing circuit operable with the blood tubing and the transmitter to send the signal.

15. The access disconnect system of claim 9, which includes a current impedance circuit operable with the blood tubing and the transmitter to send the signal.

16. The access disconnect system of claim 9, wherein the transmitter is positioned at the access site of the patient.

17. An access disconnect system comprising:
   blood tubing including a blood filter and an arterial tubing side of the blood filter;
   a blood processing machine including a blood pump operable with the blood tubing;
   first and second conductive contacts in the blood tubing on an arterial tubing side of the blood filter, the first conductive contact located upstream of the blood pump, and the second conductive contact located downstream of the blood pump, the first and second conductive contacts positioned and arranged to enable a conductive circuit to be formed with a vascular system of a patient and the blood processing machine;
   a source of electric current connected to at least one of the first and second conductive contacts;
   a sensor configured to sense an amount of electric current flowing through the conductive circuit when the source of electric current is applied; and
   wherein the blood processing machine is configured to receive and process a signal indicative of an amount of current sensed by the sensor flowing through the conductive circuit when the source of electric current is applied.

18. The access disconnect system of claim 17, which includes a transmitter for sending the signal to the blood processing machine.

19. The access disconnect system of claim 17, wherein the sensor includes a non-contact sensor for positioning atop an access site of the patient, near the vascular system of the patient, or near the blood tubing, the non-contact sensor configured for sensing the amount of electric current, and wherein the transmitter is operably connected to the non-contact sensor.

20. The access disconnect system of claim 17, wherein the source of electrical current is a time-varying source.

* * * * *